United States Patent [19]

Lin

[11] Patent Number: 4,602,088

[45] Date of Patent: Jul. 22, 1986

[54] PREPARATION OF ENAMINES FROM CONJUGATED DIENES

[75] Inventor: Jiang-Jen Lin, Round Rock, Tex.

[73] Assignee: Texaco Inc., White Plains, N.Y.

[21] Appl. No.: 634,925

[22] Filed: Jul. 26, 1984

[51] Int. Cl.$^4$ .................... C07C 85/08; C07D 295/02
[52] U.S. Cl. .................................. 544/178; 544/404;
564/408; 564/445; 564/467
[58] Field of Search ................ 544/178, 404; 564/408,
564/445, 467

[56] References Cited

U.S. PATENT DOCUMENTS

| | | | |
|---|---|---|---|
| 4,064,145 | 12/1977 | Taylor | 568/454 |
| 4,096,150 | 6/1978 | Berthoux et al. | 260/293.32 |
| 4,130,590 | 12/1978 | Hobbs et al. | 564/408 |
| 4,250,115 | 2/1981 | Imai | 564/436 |
| 4,292,242 | 9/1981 | Laine | 260/326.8 |
| 4,356,334 | 10/1982 | Imai | 568/909 |
| 4,533,751 | 8/1985 | Cherney et al. | 564/408 |

OTHER PUBLICATIONS

Stork et al., "The Enamine Alkylation and Acylation of Carbonyl Compounds", JACS, 85, 207 (1963).
Nomura et al., "Reaction Between Enamines and Schiff Bases. Evidence for the Thermal [2+2] Cycloaddition Reaction", Bull. Chem. Soc. Japan, 55, 3343-3344 (1982).
Ishihara et al., "a-Pentafluoropropionylation of Ketones and Aldehydes Using Hexafluoropropene Oxide. A Facile Synthesis of Fluorinated 1,3-Diketones", Bull. Chem. Soc. Jpn., 55, 3345-3346, 1982.
Allen, "The Synthesis of 5-Hydroxyindoles by the Nenitzescu Reaction", Organic Reactions, vol. 20, Ch. 3, pp. 337-345.
Jachimowicz et al., "Scope and Pathway of Catalytic Aminomethylation of Olefins", J. Org. Chem., 1982, 47, 445-447.
Laine, "Catalysis of the Aminomethylation Reaction. Enhanced Catalytic Activity with Mixed-Metal Catalysts. Applications of the Water-Gas Shift Reaction," J. Org. Chem., 1980, 45, 3370-3372.

Primary Examiner—Robert W. Ramsuer
Attorney, Agent, or Firm—Jack H. Park; Kenneth R. Priem

[57] ABSTRACT

A method for the preparation of enamines wherein a conjugated diene is reacted with a secondary amine, carbon monoxide and hydrogen (synthesis gas) in solvent solution in the presence of a rhodium catalyst. In accordance with the preferred embodiment, butadiene is reacted with a dialkylamine and synthesis gas in an organic solvent in the presence of a rhodium catalyst to provide the corresponding 1,3-pentadienyl dialkylamine in good yield and with good selectivity. This may be illustrated, for example, by the following equation:

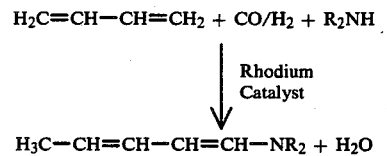

7 Claims, No Drawings

PREPARATION OF ENAMINES FROM CONJUGATED DIENES

BACKGROUND OF THE INVENTION

1. Technical Field of the Invention

This invention relates to the manufacture of enamines from conjugated dienes. More particularly, this invention relates to a method wherein a conjugated diene, such as 1,3-butadiene is reacted with a secondary amine and also with carbon monoxide and hydrogen (synthesis gas) at an elevated temperature and under appropriate pressure in the presence of a rhodium-containing catalyst to substantially selectively convert the conjugated diene to an enamine.

2. Prior Art

It is known that organic amines can be prepared from enamines by Diels-Alder reactions, Michael-type reactions, reduction reactions, etc. There is a need, therefore, for improved methods for the preparation of enamines.

The enamines are versatile intermediates in organic synthesis, for example, a general method for preparing enamines from a carbonyl compound, an aldehyde or ketone, with a secondary amine and the synthetic applications of enamines such as alkylation or acylation have been reported by G. Stork et al., JACS, 85, 207 (1963). Review articles, Tetrahedron, 33, 609 (1977) and Tetrahedron, 38, 3363 (1982), cover developments in the methods of preparation of enamines and the reaction of enamines with electrophiles.

Nomura et al. (*Bull. Chem. Soc. Jpn.* 55, 3343–3344, 1982) disclose the reaction between enamines and Schiff Bases by a cyclo addition reaction such as the reaction between N-benzylideneanilines and 4-(1-phenyl-1-propenyl)morpholine to provide N-(3-aryl-2-methyl-1-phenylallylidene)anilines.

Ishihara et al. (*Bull. Chem. Soc. Jpn* 55, 3345–3346, 1982) disclose the preparation of enamines from ketones and aldehydes to provide morpholine enamines which are then reacted with hexafluoropropene oxide to provide pentafluorinated 1,3-diketones.

The preparation and reaction of enamines is discussed in Chapter 3 of Volumne 20 of *Organic Reactions* in an article by George R. Allen, Jr. entitled "The Synthesis of 5-Hydroxyindoles by the Nenitzescu Reaction".

The related synthesis gas reactions of olefins, amines and $CO/H_2$ in the presence of various catalysts, such as rutheninum, cobalt, iron and rhodium, generally produced amines as the products (namely, aminomethylation). Some examples are discussed as follows. In U.S. Pat. No. 4,292,242 and J. Org. Chem., 1980, 45, 3370–3372, R. M. Laine disclosed the synthesis of tertiary amines from olefins, carbon monoxide, water and amines by using mixed metal hydroformylation catalysts. U.S. Pat. Nos. 4,250,115; 4,356,334 and 4,096,150 and J. Org. Chem., 1982, 47, 445–447, describe the synthesis of tertiary and secondary amines from olefins, carbon monoxide, hydrogen or water and a nitrogen source in the presence of transition-metal compounds as catalysts, including rhodium.

The synthesis of dienamines intermediately from the reaction of butadiene, an amine, and $CO/H_2$ using a rhodium catalyst under mild pressure and temperature has not been disclosed.

SUMMARY OF THE INVENTION

The present invention is directed to a method for the preparation of enamines wherein a conjugated diene is reacted with a secondary amine, carbon monoxide and hydrogen (synthesis gas) in solvent solution in the presence of a rhodium catalyst. In accordance with the preferred embodiment, butadiene is reacted with a dialkylamine and synthesis gas in an organic solvent in the presence of a rhodium catalyst to provide the corresponding 1,3-pentadienyl dialkylamine in good yield and with good selectivity. This may be illustrated, for example, by the following equation:

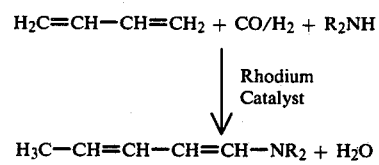

DETAILED DESCRIPTION

The Starting Materials

The starting materials for the present invention include a conjugated diene, a secondary amine, synthesis gas, a rhodium catalyst and an organic solvent.

Any appropriate conjugated diene may be utilized for the practice of the invention including, but not limited to, 1,3-butadiene, isoprene, (2-methyl-1,3-butadiene), 1-methyl-1,3-butadiene, 2,3-dimethyl-1,3-butadiene, etc.

A wide variety of secondary amines may be used alone, or in admixture, as feedstocks, depending upon the nature of the desired enamine product that is desired. Thus, dialkylamines, diarylamines, cyclic amines, heterocyclic amines, etc. may be used such as, for example, dimethylamine, diethylamine, dipropylamine, diisopropylamine, diallylamine, dibutylamine, diisobutylamine, ethyl-n-butylamine, di-n-amylamine, dicyclohexylamine, etc., N-methylaniline, N-ethylaniline, diphenylamine, 2-methyldiphenylamine, 4,4'-dimethyldiphenylamine, 2,2'-diethyldiphenylamine, 4,4'-dioctyldiphenylamine, N-phenyl-1-naphthylamine, etc., morpholine, 2-methylmorpholine, N-methylpiperizine, etc.

A rhodium catalyst is used in accordance with the present invention. Any rhodium-containing compound capable of forming a carbonyl under the reaction conditions can be used. This rhodium compound may be a carbonyl such as hexarhodium hexadecacarbonyl. Preferably, the rhodium carbonyl is complexed with a phosphine ligand. Such catalysts are described in U.S. Pat. Nos. 4,064,145; 4,400,548 and 4,400,549, the pertinent portions of which are incorporated by reference herein. It is especially preferred that the catalyst be a rhodium carbonyl triphenylphosphine complex catalyst such as hydridocarbonyltris(triphenylphosphine)rhodium(I). This complex may be written as $HRh(CO)(PPh_3)_3$, where Ph represents a phenyl group. Preferably, an excess of the phosphine ligand is added to provide additional triphenylphosphine.

An inert, organic solvent is employed. Preferred organic solvents such as ethers, ketones and tertiary amines including diethyl ether, p-dioxane, tetraglyme, methyl iso-butyl ketone, 2-undecanone, triethylamine and tri-n-propylamine. Inert, non-polar compounds are also useful as solvents, such as, for example, alkanes, such as hexanes, hexadecane, aromatics such as benzene, toluene, ortho-xylene, meta-xylene, para-xylene, mixed xylenes, ethylbenzene, etc. and mixtures thereof.

The temperature range which can be employed is a variable which is dependent upon experimental factors including the particular feedstocks employed, the total pressure, the mole ratio of hydrogen and carbon monoxide used, the concentrations of reactants and catalyst, among other things. Using 1,3-butadiene as a feedstock and rhodium carbonyl-triphenylphosphine complex as a representative catalyst, an operable range is from about 20° C. to 150° C. or more when superatmospheric pressures of greater than 100 psig are employed. A narrower range of 50° C. to 120° C. represents the preferred temperature range.

The pressure range which can be employed is a variable which is also dependent on the factors mentioned above. Using rhodium carbonyl-triphenylphosphine as a representative catalyst and 1,3-butadiene as the feedstock, an operable pressure range is from about 100 to 5,000 psig or more, with a mole ratio of $H_2/CO$ being 1:1 when a temperature range of from about 20° C. to 150° C. is employed. A narrower range of from 500 to 1,500 psig represents the preferred pressure range when the narrower temperature range of 50° C. to 120° C. is employed.

The $H_2/CO$ mole ratio may be varied over a range of from 30:1 to 1:30 when suitable temperatures and pressures are employed. A preferred narrower range is from 2:1 to 1:2 of hydrogen/carbon monoxide.

The amine/butadiene molar ratio may be varied over a range of 3:1 to 1:3 and the rhodium catalyst concentration can be at the range of 50 ppm to 5% based on the total starting material used. A preferred narrower range for amine/butadiene is a 1:1 ratio and for the rhodium catalyst, concentrations of 200 ppm to 2000 ppm.

Conversion as defined herein represents the extent of conversion of the reacting amines to other products. Conversion is expressed as a percentile and is calculated by dividing the amount of amines consumed by the amount of amines originally charged and multiplying the quotient by 100.

Yield, as defined herein, represents the efficiency in catalyzing the desired reaction relative to other undesired reactions. Yield is expressed as a percentile and is calculated by determining the amount of enamine product formed, divided by the amount of amines charged and multiplying the quotient obtained by 100.

Selectivity, as defined herein, is the efficiency in catalyzing a desired reaction relative to the other undesired conversion. Selectivity is expressed as a percentile and is calculated by determining the amount of enamine product formed, divided by the total amount of products formed and multiplying the quotient obtained by 100.

The invention will be further illustrated by the following specific examples which are given by way of illustration and not as limitations on the scope of this invention.

SPECIFIC EXAMPLES

Example 1

To a 300 ml stainless-steel, magnedrive reactor was charged $HRh(CO)(PPh_3)_3$ (0.092 g, 0.1 mmole), triphenylphosphine (2.6 g, 10 mmole) diethylamine (7.3 g, 100 mmole) and toluene (20.0 g). The reactor was sealed and purged of air with a mixture of carbon monoxide and hydrogen ($CO/H_2=1:2$). Then butadiene (ca. 17.0 g) was charged by purging with mixtures of carbon monoxide and hydrogen. The initial pressure (butadiene plus syngas) was 150 psi. The temperature was brought up to 110° C. and the pressure was increased to 800 psi with addition of the mixture of carbon monoxide and hydrogen ($CO/H_2=1:2$). During the process of reaction, syngas was supplied through a surge tank in order to maintain 800 psi pressure. After 3 hours reaction time, the reactor was cooled to room temperature and excess gas was vented, following which 41.0 g yellow solution with a ca. 0.5 g bottom layer (water) was recovered. The glc analysis showed a product peak at ca. 74% selectivity and the conversion of diethylamine was >95%. The pure product was isolated by flash distillation and H'-nmr showed 5.9δ(m, 2H, olefinic, 5.0δ(m, 2H, olefinic) 2.9δ(m, 4H, —N—$CH_2$—), 1.7δ(two d, 3H, $CH_3$—C=C) and 1.0δ(m, 6H, —N—C—$CH_3$); $c^{13}$ nmr showed three alkane peaks at 13, 18 and 45 ppm plus two sets of olefinic carbon at the range of 95–140 ppm. The structure was assigned as:

$$CH_3CH=CHCH=CHN(CH_2CH_3)_2$$

There are two isomeric cis-trans diene structures based on $C^{13}$ data.

The results with various reaction conditions and starting amines are outlined in Table I.

TABLE I

Reactions of Butadiene, Syngas and Amines Catalyzed by Rh[1,2]

| Example | Starting Amines | Butadiene (Charged) (g) | Solvent | Reaction Conditions | Product[3] Selectivity (%) | Weight Recovery (g) | Notes |
|---|---|---|---|---|---|---|---|
| 1 | $Et_2NH$ (7.3 g) | 17 | Toluene (20 g) | 93–114° C.; 800 psi $CO/H_2$ 1:2; 3 hr. | 74 | 41.5 | Yellow solution |
| 2 | $Et_2NH$ (7.3 g) | 20 | p-dioxane (20 g) | 100–105° C.; 800 psi $CO/H_2$ 1:1; 4 hr. | 76 | 45.5 | Light brown solution |
| 3 | $Et_2NH$ (7.3 g) | 13 | p-dioxane (20 g) | 142–156° C.; 800 psi $CO/H_2$ 1:2; 4 hr. | <10 | 47.0 | Brown solution |
| 4 | $Et_2NH$ (7.3 g) | 20 | p-dioxane (20 g) | 105° C.; 800 psi $CO/H_2$ 1:2; 2 hr. | 75 (45% conv. at 1 hr.) | 52.9 | Brown solution |
| 5 | Morpholine (8.6 g) | 12 | Toluene (20 g) | 86–120° C.; 800 psi $CO/H_2$ 1:2; 5.5 hr. | 88 | 36.5 | Light brown solution |
| 6 | $n-PrNH_2$ | 25 | p-dioxane (20 g) | 100–112° C.; 800 psi | No major 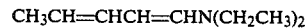 | 49.0 | Deep red |

TABLE I-continued
Reactions of Butadiene, Syngas and Amines Catalyzed by Rh[1,2]

| Example | Starting Amines | Butadiene (Charged) (g) | Solvent | Reaction Conditions | Product[3] Selectivity (%) | Weight Recovery (g) | Notes |
|---------|-----------------|-------------------------|---------|---------------------|---------------------------|---------------------|-------|
|         | (5.9 g)         |                         |         | $CO/H_2$ 1:2        | products                  |                     | solution |

[1]Catalyst: HRh (CO)(PPh$_3$)$_3$ (0.092 g, 0.1 mm) and Ph$_3$P (2.6 g)
[2]Amine conversion: >95% except as noted

[3]Product: $CH_3CH=CHCH=CHNR_2$ (where $-NR_2 = -NEt_2$ or  )

Example 6

To a 300 ml stainless-steel, magnedrive reactor was charged with HRh(CO)(PPh$_3$)$_3$ (0.092 g, 0.1 mmole), triphenylphosphine (2.6 g), n-propylamine (5.9 g, 0.1 mole), p-dioxane (20.0 g). The reactor was sealed and purged with synthesis gas. The butadiene (25.0 g) was charged and 200 psi of CO/H$_2$ (1:2 molar ratio) was added. The temperature was brought up to ~105° C. and the pressure to 800 psi by CO/H$_2$=1:2 mixture. The reaction condition was held for ~5 hours. During the process, the pressure uptake was noticed. The reactor was cooled to room temperature and excess gas was vented off. A deep-red solution was obtained (49.0 g). The analysis showed 100% of n-propylamine conversion, but there was no major product detected by glc.

Thus, a primary amine is not a suitable amine compared with secondary amine (i.e., diethylamine or morpholine).

Having thus described my invention, what is claimed is:

1. A method for preparing an enamine having conjugated olefinic unsaturation which comprises reacting a conjugated diene with a secondary amine, hydrogen and carbon monoxide at a temperature within the range of about 20° to about 150° C. and a pressure within the range of about 100 to about 5000 psig, in organic solvent solution in the presence of rhodium carbonyl catalyst complexed with a phoshine ligand.

2. A method as in claim 1 wherein the molar ratio of hydrogen to carbon monoxide is within the range of about 30:1 to about 1:30.

3. A method for preparing 1,3-pentadienylamine which comprises reacting butadiene with about an equimolar amount of a secondary amine in organic solvent solution in the presence of hydrogen and carbon monoxide and a rhodium carbonyl catalyst complexed with a phosphine ligand at a temperature within the range of about 50° to about 120° C. and a pressure within the range of about 500 to about 1,500 psig, the molar ratio of hydrogen to carbon monoxide being within the range of about 2:1 to about 1:2.

4. A method as in claim 3, wherein the secondary amine is a dialkylamine.

5. A method as in claim 4, wherein the dialkylamine is diethylamine.

6. A method as in claim 3, wherein the secondary amine is a heterocyclic amine.

7. A method as in claim 6, wherein the heterocyclic amine is morpholine.

* * * * *